United States Patent
Reierson et al.

(10) Patent No.: US 10,238,595 B2
(45) Date of Patent: Mar. 26, 2019

(54) ABLATIVE, RENEWABLE, MULTI-FUNCTIONAL PROTECTIVE COATING FOR DENTAL SURFACES

(71) Applicant: RHODIA OPERATIONS, Paris (FR)

(72) Inventors: Robert Lee Reierson, Princeton Junction, NJ (US); Denis Bendejacq, New Brunswick, NJ (US)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 15/807,711

(22) Filed: Nov. 9, 2017

(65) Prior Publication Data

US 2018/0064625 A1     Mar. 8, 2018

Related U.S. Application Data

(62) Division of application No. 14/940,804, filed on Nov. 13, 2015, now Pat. No. 9,839,599.

(60) Provisional application No. 62/079,001, filed on Nov. 13, 2014, provisional application No. 62/078,996, filed on Nov. 13, 2014.

(51) Int. Cl.
  *A61K 8/81*  (2006.01)
  *C07F 9/09*  (2006.01)
  *A61Q 11/00*  (2006.01)
  *C07F 9/572*  (2006.01)

(52) U.S. Cl.
  CPC ............ *A61K 8/817* (2013.01); *A61K 8/8164* (2013.01); *A61Q 11/00* (2013.01); *C07F 9/091* (2013.01); *C07F 9/572* (2013.01); *A61K 2800/28* (2013.01)

(58) Field of Classification Search
  CPC ...................................................... A61K 8/81
  USPC .............................................. 424/49; 522/63
  See application file for complete search history.

(56) References Cited

U.S. PATENT DOCUMENTS

| | | | |
|---|---|---|---|
| 2,980,652 A | 4/1961 | Melamed et al. | |
| 5,306,828 A | 4/1994 | Adda et al. | |
| 5,550,274 A | 8/1996 | Reierson | |
| 5,605,676 A | 2/1997 | Gaffar et al. | |
| 6,110,445 A | 8/2000 | Gaffar et al. | |
| 6,555,593 B1 * | 4/2003 | Hoyle | C08F 2/50 522/166 |
| 8,653,181 B2 | 2/2014 | Trezzi et al. | |
| 9,034,308 B2 | 5/2015 | Reierson et al. | |
| 9,040,025 B2 | 5/2015 | Reierson et al. | |
| 9,115,236 B2 | 8/2015 | Adam et al. | |
| 2008/0247973 A1 | 10/2008 | Baig et al. | |
| 2009/0169493 A1 | 7/2009 | Reierson et al. | |
| 2009/0238775 A1 | 9/2009 | Futterer et al. | |
| 2010/0316579 A1 | 12/2010 | Fowler et al. | |
| 2012/0028856 A1 | 2/2012 | Adam et al. | |
| 2012/0029138 A1 | 2/2012 | Martinez-Castro et al. | |

FOREIGN PATENT DOCUMENTS

| | | |
|---|---|---|
| JP | 2007284609 A2 | 11/2007 |
| WO | 2010004361 A2 | 1/2010 |

OTHER PUBLICATIONS

J. Olsson, et al., "Inhibition of *Streptococcus mutans* Adherence to Hydroxyapatite with Combinations of Alkyl Phosphates and Nonionic Surfactants", Caries Res. 1991; 25:51-57, S. Karger AG, Basel.

M. Hirao, et al., "Resonance EMAT system for acoustoelastic stress measurement in sheet metals", Review of Instruments 64 (11): 3198-3205, 1993, AIP Publishing Scientific.

M. Rodahl, et al., "A simple setup to simultaneously measure the resonant frequency and the absolute dissipation factor of a quartz crystal microbalance", Review of Scientific Instruments 67 (9) 3238-3241, 1996, AIP Publishing.

D. Johannsmann, "Viscoelastic mechanical, and dielectric measurements on complex samples with the quartz crystal microbalance", Physical Chemistry Chemical Physics 10 (31): 4516-4534, 2008.

G.K. Stookey, et al., "In vitro Removal of Stain with Dentrifrices", J. Dent. Res. 61 (11): 1236-1239, 1982.

Bissette, Andrew J. et al.: "Physical autocatalysis driven by a bond-forming thiol-ene reaction", Nature Communications, vol. 5, No. 4602, Sep. 2, 2014, pp. 1-8.

* cited by examiner

*Primary Examiner* — Walter E Webb

(57) ABSTRACT

An oral care composition in the form of a toothpaste, tooth gel, dentifrice, tooth powder, prophy paste, mouthwash, rinse, tooth mousse, dental floss, chewing gum, soluble oral care strip or film for direct application or attachment to an oral surface, or lozenge for combating dental caries, erosion, hypersensitivity, and/or staining that includes an orally acceptable carrier and a copolymer of a first α, β-ethylenically unsaturated phosphate compound (A); and one or more α, β-ethylenically unsaturated co-monomers, at least one of which is other than an allyl-functional co-monomer, wherein (A) is an allyl phosphate compound of formula (A):

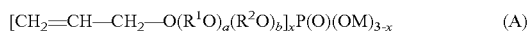

$$[CH_2=CH-CH_2-O(R^1O)_a(R^2O)_b]_xP(O)(OM)_{3-x} \quad (A)$$

wherein, $R^1$ is a substituted or unsubstituted ($C_2$-$C_4$) alkylene moiety; $R^2$ is a substituted or unsubstituted ($C_2$-$C_4$) alkylene moiety; M is identical or different, hydrogen, alkali metal, ammonium, protonated alkyl amine, protonated alkanolamine, or protonated basic amino acid; X is 1 or 2, a is from 1 to 20; and b is from 0 to 20. Methods for combating dental caries, erosion, hypersensitivity, and/or staining are also provided.

4 Claims, No Drawings

ABLATIVE, RENEWABLE, MULTI-FUNCTIONAL PROTECTIVE COATING FOR DENTAL SURFACES

RELATED APPLICATION AND CLAIM OF PRIORITY

This application is a divisional of U.S. patent application Ser. No. 14/940,804, filed Nov. 13, 2015, which claims priority to U.S. Provisional Patent Application Nos. 62/078,996 and 62/079,001, both filed on Nov. 13, 2014. The disclosures of all of these applications are incorporated into this document by reference in their entireties.

BACKGROUND

Teeth are subject to various diseases and problems, among which are caries, plaque, tartar, gingivitis, abusive whitening practices from use of concentrated hydrogen peroxide, hypersensitivity, and enamel staining.

Most oral care diseases originate with the thin proteinaceous film deposited as pellicle onto tooth surfaces. This serves as a substrate for bacteria and mineral deposits which harden into plaque and eventually tartar. The bacterial colonies sheltered therein absorb and metabolize nutrients from substances that pass through the oral cavity, particularly sucrose, and produce carboxylic acids. These acids are not readily rinsed away by the oral fluids because the colonies are protected and held in close proximity to the tooth surfaces by the plaque film. The acids produced, then, are held against the dental surfaces, where they slowly demineralize and destroy the hydroxyapatite crystal structure, producing caries. The calculus and tartar deposits cause separation of the gingival tissue from the tooth, causing inflammation and creating "pockets" which also provide a more sheltered, difficult to clean area for the destructive process. The receding gingiva eventually expose the dentinal tubules, which results in hypersensitivity.

Other, more esthetic problems are halitosis and tooth staining. The former is assuaged by treatment with flavorants, mouth fresheners and anti-bacterial agents in the toothpaste or mouthwash formulation. Anti-bacterial agents, such as triclosan and cetylpyridinium chloride, also kill cariogenic bacteria, hence serve an anti-caries function as well.

Separately, cetylpyridinium chloride, along with tea, coffee, wine, cigarette smoke and other factors may contribute to tooth staining. The popular methods of removing the stains are use of a more abrasive toothpaste formulation and/or a "whitening agent", commonly hydrogen peroxide. The concentration of the peroxide is steadily increasing in response to consumers' desire for more rapid and complete stain and discoloration removal. The problem associated with these treatments is that the more abrasive toothpaste also wears down the tooth enamel and the peroxide also oxidizes the amelogenin matrix that controls the orderly formation of the hydroxyapatite crystals in the natural remineralization process. The more aggressive peroxide treatments have been associated with development of tooth hypersensitivity.

Simple organic phosphate ester surfactants have been shown to provide numerous oral care benefits, as described, for example, in U.S. Pat. Nos. 9,034,308 and 9,040,025 and references cited therein. Such esters have been shown to be effective cleaning agents for the removal of dental surface residues and form protective films that inhibit the adherence of *Streptococcus mutans* to hydroxyapatite. *Caries Res.* 1991; 25:51-57. Phosphate ester surfactants improve the efficacy of the anti-bacterial agents, such as triclosan, by enhancing its deposition and retention onto the tooth. U.S. Pat. Nos. 5,605,676, and 6,110,445. Similarly, phosphate ester surfactants have been claimed as an essential ingredient in a formulation with the milder carbamoyl peroxide as a potential replacement for hydrogen peroxide in toothpaste and mouthwash formulations. U.S. Publication No. 2009/0169493. The integrity of the phosphate ester surfactant films on hydroxyapatite was demonstrated by their ability to protect it from erosion by citric acid (fruit juices) and phosphoric acid (cola soft drinks). U.S. Publication Nos. 2008/0247973 and 2010/0316579.

JP 2007/284609 describes copolymers based solely on phosphate ester functional (meth)acrylic ester monomers, Monomer A (e.g. the phosphate ester of 2-hydroxyethyl methacrylate), the comonomers being selected from a wide variety of non-phosphate functional monomers, "B", "C" and "D", as being useful for stain prevention and inhibition of bacterial or proteinaceous film deposition onto the tooth surface.

Although the overall effectiveness of the phosphate ester surfactants to minimize or eliminate the above problems is good, the duration of the protection is limited by the structure. Both the monoalkyl and dialkyl phosphate esters have only a single phosphate ester moiety to serve as the point of attachment to the dental surface. The oral phosphatase enzymes can penetrate the surfactant film to eventually hydrolyze the phosphate ester link and destroy the film over a period estimated to be about six to eight hours. To be more in line with personal oral hygiene practices of once daily tooth brushing, it would be desirable to at least double this period of effectiveness and further improve the film integrity, durability and resistance to penetration.

SUMMARY

The present disclosure provides an oral care composition in the form of a toothpaste, tooth gel, dentifrice, tooth powder, prophy paste, mouthwash, rinse, tooth mousse, dental floss, chewing gum, soluble oral care strip or film for direct application or attachment to an oral surface, or lozenge for combating dental caries, erosion, hypersensitivity, and/or staining that includes an orally acceptable carrier and a copolymer of a first α, β-ethylenically unsaturated phosphate compound (A); and one or more α, β-ethylenically unsaturated co-monomers, at least one of which is other than an allyl-functional co-monomer, wherein (A) is an allyl phosphate compound of formula (A):

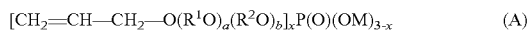
$$[CH_2=CH-CH_2-O(R^1O)_a(R^2O)_b]_xP(O)(OM)_{3-x} \quad (A)$$

wherein, $R^1$ is a substituted or unsubstituted ($C_2$-$C_4$) alkylene moiety; $R^2$ is a substituted or unsubstituted ($C_2$-$C_4$) alkylene moiety; M is identical or different, hydrogen, alkali metal, ammonium, protonated alkyl amine, protonated alkanolamine, or protonated basic amino acid; X is 1 or 2, a is from 1 to 20; and b is from 0 to 20.

Also described is an α, β-ethylenically unsaturated maleimide phosphate compound of the formula (B):

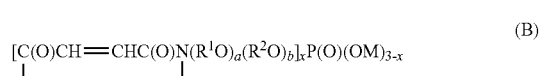
$$[C(O)CH=CHC(O)N(R^1O)_a(R^2O)_b]_xP(O)(OM)_{3-x} \quad (B)$$

wherein: $R^1$ is a substituted or unsubstituted ($C_2$-$C_4$) alkylene moiety; $R^2$ is a substituted or unsubstituted ($C_2$-$C_4$)

alkylene moiety; M is identical or different, hydrogen, alkali metal, ammonium, protonated alkyl amine, protonated alkanolamine, or protonated basic amino acid; X is 1 or 2, a is from 1 to 20; and b is from 0 to 20.

Oral care compositions incorporating the copolymers of the present disclosure and methods for combating dental caries, erosion, hypersensitivity, and/or staining by contacting a dental surface with an oral care composition are also disclosed.

DETAILED DESCRIPTION

While specific embodiments are discussed, the specification is illustrative only and not restrictive. Many variations of this disclosure will become apparent to those skilled in the art upon review of this specification.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In general, compositions according to the present disclosure include oral care compositions in the form of a toothpaste, tooth gel, dentifrice, tooth powder, prophy paste, mouthwash, rinse, tooth mousse, dental floss, chewing gum, soluble oral care strip or film for direct application or attachment to an oral surface, or lozenge for combating dental caries, erosion, hypersensitivity, and/or staining that include an orally acceptable carrier and a copolymer, the copolymer being of a first α, β-ethylenically unsaturated phosphate compound (A); and one or more α, β-ethylenically unsaturated co-monomers, at least one of which is other than an allyl-functional co-monomer, wherein (A) is an allyl phosphate compound of formula (A)

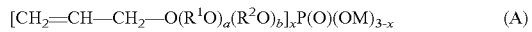

$$[CH_2=CH-CH_2-O(R^1O)_a(R^2O)_b]_xP(O)(OM)_{3-x} \quad (A)$$

wherein
$R^1$ is a substituted or unsubstituted ($C_2$-$C_4$) alkylene moiety;
$R^2$ is a substituted or unsubstituted ($C_2$-$C_4$) alkylene moiety;
M is identical or different, hydrogen, alkali metal, ammonium, protonated alkyl amine, protonated alkanolamine, or protonated basic amino acid;
X is 1 or 2,
a is from 1 to 20; and
b is from 0 to 20.

In some embodiments, the copolymer has a molecular weight and functionality selected so that the copolymer forms a film which protects a dental surface from attachment of bacteria, plaque, and staining agents while enhancing the deposition and retention of fluoride, anti-bacterial agents and/or gentle tooth whiteners onto the dental surface.

In some embodiments the one or more instances of $R^1$ and/or $R^2$ in the compound of formula (A) are substituted with a hydroxy, alkoxy or aryloxy moiety.

In some embodiments, one or more instances of the ($C_2$-$C_4$) alkylene moiety in formula (A) is substituted with a hydroxy, alkoxy or aryloxy moiety.

The first α, β-ethylenically unsaturated phosphate compound (allyl phosphate compound) of formula (A) can be prepared by known methods. For example, U.S. Pat. No. 8,653,181, incorporated herein by reference in its entirety, describes methods for preparing allyl ethoxylate phosphate ester embodiments of formula (A).

The α, β-ethylenically unsaturated co-monomers may be any such compound but preferably monomers that copolymerize well with allyl monomers and may include those different from monomer (A) but still contain phosphate or other functional groups, such as carboxylate, or sulfonate. In some embodiments, one or more of the α, β-ethylenically unsaturated co-monomers is an allyl functional sulfonate monomer such as, for example, sodium 1-allyloxy-2-hydroxypropyl sulfonate or a non-allyl monomer, sodium 2-acrylamido-2-methylpropane sulfonate, sodium vinyl sulfonate, sodium styrene sulfonate, acrylic acid or methacrylic acid, maleic acid, maleic anhydride (optionally, as its anhydride that is hydrolyzed post-polymerization), fumaric acid, itaconic acid and their water soluble salts, particularly their alkali metal or ammonium salts, as described in U.S. Pat. No. 9,115,236, incorporated herein by reference. In some embodiments, one or more of the α, β-ethylenically unsaturated co-monomers is an allyl ethoxylate or methallyl ethoxylate. In some embodiments, one or more of the α, β-ethylenically unsaturated co-monomers is a compound according to formula (B), which is described below. In some embodiments, one or more of the α, β-ethylenically unsaturated co-monomers is selected from combinations of any of the above-mentioned co-monomers.

Although the acidic, ionic monomers may be copolymerized in either the acid or salt form, it is understood that it would be necessary to adjust the pH of the final copolymer to physiological pH, hence at least partially converting the acidic groups to the salt forms.

Co-monomers are preferably selected and the polymerization process chosen to maximize incorporation of the monomers into the copolymer according to the desired distribution: random, alternating or in blocks. Preferably, the "-mer" units are distributed as evenly as possible along the polymer chain.

In some embodiments the first α, β-ethylenically unsaturated phosphate compound (A), is an allyl phosphate compound of formula (A-1) wherein n is 1 to 20 (preferably 3 to 4):

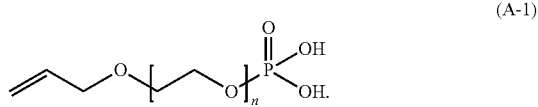

(A-1)

As mentioned above, in some embodiments, one or more of the α, β-ethylenically unsaturated co-monomers is an α, β-ethylenically unsaturated maleimide phosphate compound of the formula (B):

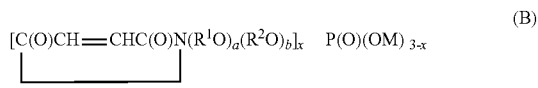

$$[C(O)CH=CHC(O)N(R^1O)_a(R^2O)_b]_x \quad P(O)(OM)_{3-x} \quad (B)$$

wherein
$R^1$ is a substituted or unsubstituted ($C_2$-$C_4$) alkylene moiety;
$R^2$ is a substituted or unsubstituted ($C_2$-$C_4$) alkylene moiety;
M is identical or different, hydrogen, alkali metal, ammonium, protonated alkyl amine, protonated alkanolamine, or protonated basic amino acid;

X is 1 or 2,
a is from 1 to 20; and
b is from 0 to 20.

In some embodiments the one or more instances of $R^1$ and/or $R^2$ in the compound of formula (B) are substituted with a hydroxy, alkoxy or aryloxy moiety.

In some embodiments, non-ionic monomers are used to balance the reactivities of the selected monomer mixtures and influence bulk properties of the copolymer, such as water solubility, $T_g$, toughness, durability or cost. These would include vinyl acetate, acrylate esters, methacrylate esters, maleate esters and diesters, fumarate diesters and styrene.

In some embodiments, at least one of the co-monomers is a non-ionic maleimidoalkoxylate co-monomer compound of formula (C):

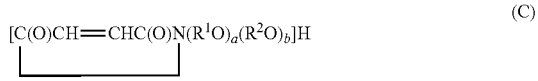

(C)

wherein
$R^1$ is a substituted or unsubstituted ($C_2$-$C_4$) alkylene moiety;
$R^2$ is a substituted or unsubstituted ($C_2$-$C_4$) alkylene moiety;
a is from 1 to 20; and
b is from 0 to 20.

In some embodiments one or more instances of the ($C_2$-$C_4$) alkylene moiety is substituted with a hydroxy, alkoxy or aryloxy moiety.

An example of a suitable non-ionic maleimide alkoxylate comonomer compound is of the formula (C-1):

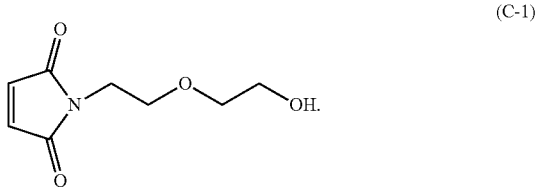 [SMILES: O=C1C=CC(=O)N1CCOCCO]

(C-1)

The maleimide derivatives may be prepared by reacting the proper primary amine with maleic anhydride as reported in U.S. Pat. No. 5,306,828. The monomer (C-1) can be set aside from the bulk of the maleimide for later use or a portion of the total charge could be phosphated with a reduced phosphation reagent charge, leaving excess (C-1) in the phosphate product mixture as a "non-ionic" monomer of similar polymerization reactivity and a terminal hydroxyl group compatible with the other comonomers. It would serve as a "diluent" monomer that could reduce the phosphate monomer content in the copolymer if that were desired.

Copolymers and terpolymers of additional ethylenically unsaturated monomers and the allyl alkoxylate phosphate esters of formula (A) and/or maleimide polyalkoxylate phosphate esters of formula (B) can be prepared by synthesis methods described in U.S. Pat. No. 9,115,236.

Also presented is an α, β-ethylenically unsaturated maleimide phosphate compound of the formula (B):

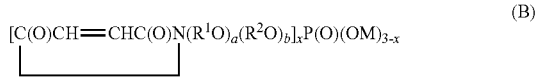

(B)

wherein
$R^1$ is a substituted or unsubstituted ($C_2$-$C_4$) alkylene moiety;
$R^2$ is a substituted or unsubstituted ($C_2$-$C_4$) alkylene moiety;
M is identical or different, hydrogen, alkali metal, ammonium, protonated alkyl amine, protonated alkanolamine, or protonated basic amino acid;
X is 1 or 2,
a is from 1 to 20; and
b is from 0 to 20.

In some embodiments the one or more instances of $R^1$ and/or $R^2$ in the compound of formula (B) are substituted with a hydroxy, alkoxy or aryloxy moiety.

The α, β-ethylenically unsaturated maleimide phosphate compound of formula (B) can be prepared by several processes. In an embodiment, 2-hydroxyethyl-2-oxyethyl amine (Diglycolamine, available from Huntsman Corporation) is reacted with an approximately equimolar amount of maleic anhydride in chloroform according to an altered version of the method described in Example 1 of U.S. Pat. No. 2,980,652, with Diglycolamine substituted for the 1-(2-aminoethyl)imadazolidinone-2 used in the example. The resultant compound is then ring closed according to an altered method of Example 5 of U.S. Pat. No. 2,980,652. In the altered version of the method, the resultant compound contains —$CH_2CH_2OCH_2CH_2OH$ in place of the imidazolidinone-2 ring in the formula at lines 40-44 of Column 10 of the '652 patent. The resultant ring-closed hydroxy-functional maleimide compound is then phosphated by reacting it with polyphosphoric acid and phosphoric anhydride according to an altered method of Example 1 of U.S. Pat. No. 5,550,274, with the hydroxy-functional maleimide compound substituted for the lauryl alcohol and adjusting the molar amount of the phosphation reagent to the specific requirements of the process.

In some embodiments the maleimide phosphate compound of formula (B) is a compound of formula (B-1):

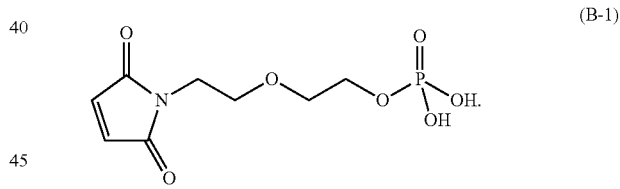

(B-1)

Also presented is a composition that includes a copolymer polymerized from a monomer mixture comprising one or more α, β-ethylenically unsaturated maleimide phosphate compounds of formula (B) and one or more α, β-ethylenically unsaturated co-monomers, at least one of which is other than maleimide-functional. In some embodiments, such compositions are oral care compositions and further include an orally acceptable carrier.

In some embodiments, one or more of the α, β-ethylenically unsaturated co-monomers polymerized with one or more compounds of formula (B) is an allyl functional sulfonate monomer such as, for example, sodium 1-allyloxy-2-hydroxypropyl sulfonate or a non-allyl monomer, sodium 2-acrylamido-2-methylpropane sulfonate, sodium vinyl sulfonate, sodium styrene sulfonate, acrylic acid or methacrylic acid, maleic acid, maleic anhydride (optionally, as its anhydride that is hydrolyzed post-polymerization), fumaric acid, itaconic acid and their water soluble salts, particularly their alkali metal or ammonium salts, as described in U.S. Pat. No. 9,115,236, incorporated herein by reference. In some embodiments, one or more of the α, β-ethylenically unsaturated co-monomers is allyl ethoxylate (or polyethoxylate) or methallyl ethoxylate (or polyethoxylate). In some embodiments, one or more of the α, β-ethylenically unsaturated co-monomers is a compound according to formula (A), which is described above. In some embodiments, one or more of the α, β-ethylenically unsaturated co-monomers is selected from combinations of any of the above-mentioned co-monomers.

In some embodiments, non-ionic monomers are used to balance the reactivities of the selected monomer mixtures and influence bulk properties of the copolymer, such as water solubility, $T_g$, toughness, durability or cost. These would include vinyl acetate, acrylate esters, methacrylate esters, maleate esters and diesters, fumarate diesters and styrene.

Although the acidic, ionic monomers may be copolymerized in either the acid or salt form, it is understood that it would be necessary to adjust the pH of the final copolymer to physiological pH, hence at least partially converting the acidic groups to the salt forms.

In some embodiments, the co-monomers are selected so that the copolymer is an alternating copolymer having essentially no homopolymerization. In some embodiments, the co-monomers are selected so that the copolymer is an alternating copolymer exhibiting a degree of homopolymerization.

In some embodiments the α, β-ethylenically unsaturated phosphate co-monomer, is an allyl phosphate compound of formula (A-1):

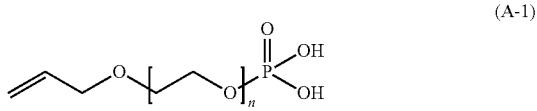

(A-1)

wherein n is 1 to 20.

In some embodiments the α, β-ethylenically unsaturated phosphate co-monomer, is an allyl compound of formula (D-1):

$$CH_2=CH-CH_2-O(CH_2CH_2O)_a-H \quad (D-1)$$

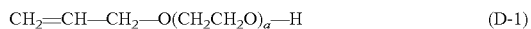

wherein a is 1 to 20.

In some embodiments, one or more of the α, β-ethylenically unsaturated co-monomers is one or more allyl functional monomers, which may be homologues of the polyalkylene oxide monoallyl ether starting materials for formula (A), formula (D):

$$[CH_2=CH-CH_2-O(R_1O)_a(R_2O)_b]_xH \quad (D),$$

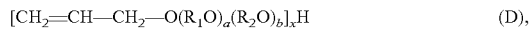

wherein $R_1$, $R_2$, a, b, and X are defined as in formula (A).

In some embodiments, one or more of the α, β-ethylenically unsaturated co-monomers is an allyl functional monomer of the formula (E):

$$CH_2=C(R^2)CH_2O(R^3)(OH)SO_3M \quad (E)$$

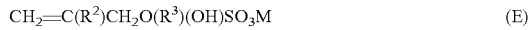

wherein
$R^2$ is H or an alkyl radical;
$R^3$ is a linear or branched substituted or unsubstituted divalent aliphatic radical; and
M is alkali metal, ammonium, protonated alkyl amine, protonated alkanolamine, or protonated basic amino acid.

In some embodiments, one or more of the α, β-ethylenically unsaturated co-monomers is selected from combinations of any of the above-mentioned co-monomers.

Also presented are oral care compositions that include one or more of any of the phosphate copolymers according to the present disclosure. Compositions according to the present disclosure are suitable for use by human and nonhuman mammals. The term "oral care composition" as used herein means a product that in the ordinary course of usage is retained in the oral cavity for a time sufficient to contact some or all of the dental surfaces and/or oral tissues for purposes of oral activity. The term "dental surface" as used herein means a surface of a natural tooth or a hard surface of artificial dentition including a denture, dental plate, crown, cap, filing, bridge, dental implant, and the like.

In some embodiments, the oral care composition is selected from toothpastes, tooth gels, dentifrices, tooth powders, prophy pastes, mouthwashes, rinses, tooth mousse, dental floss, chewing gum, soluble oral care strips or films for direct application or attachment to oral surfaces, or lozenges. In some embodiments, the oral care composition includes at least one copolymer having a molecular weight and functionality selected so that the copolymer forms a film that adheres to and protects a dental surface from acidic beverage or acid-reflux induced erosion, hypersensitivity, attachment of bacteria, plaque, and staining agents while enhancing the deposition and retention of fluoride, antibacterial or gentle whitening agents onto the dental surface.

In some embodiments, the oral care composition includes an orally acceptable carrier. In various embodiments, the carrier is a liquid, semi-solid or solid. A "liquid" can be a liquid of low or high viscosity. A liquid can be a liquid such that flow is imperceptible under ambient conditions. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPas. Carriers among those useful herein include liquids, pastes, ointments, and gels, and can be transparent, translucent or opaque. In some embodiments, the orally acceptable carrier includes water.

In some embodiments, the oral care composition includes an abrasive polishing material. In some embodiments, the abrasive polishing material is selected from silicas, aluminas, orthophosphates, polyphosphates, hexametaphosphates, and mixtures thereof. In some embodiments, the oral care composition includes one or more additives. In some embodiments, the one or more additives are selected from polishing agents, anti-bacterial agents, foaming agents, binders, humectants, medicinal agents, sweetening agents, flavors, fluoride ion sources, peroxide sources, alkali metal bicarbonate salts, thickening materials, xylitol, sorbitol, coloring agents, sodium carbonate and mixtures thereof.

In some embodiments, the oral care composition includes a safe and effective amount of a fluoride source. The fluoride source may be sufficient to provide anticaries effectiveness. A wide variety of fluoride ion-yielding materials can be employed as sources of soluble fluoride in the present oral care compositions. Representative fluoride ion sources include: sodium fluoride, potassium fluoride, sodium monofluorophosphate, and combinations thereof.

In some embodiments, the oral care composition includes an abrasive agent selected from one or more of hydrated silica, colloidal silica, fumed silica, insoluble sodium hexametaphosphate, insoluble sodium aluminosilicates, sodium bicarbonate and mixtures thereof.

In some embodiments, one or more copolymers are present in a liquid carrier.

In some embodiments, the oral care composition includes a phosphate ester surfactant. Preferred phosphate ester surfactants include those described in U.S. Pat. No. 9,040,025, the disclosure of which is incorporated herein by reference in its entirety.

In some embodiments, the oral care composition is a tooth cleaning product, which includes one or more phosphate copolymers according to the present disclosure, an abrasive agent, preferably free of calcium and other divalent ions, a surfactant, preferably a phosphate ester salt, and optionally a liquid.

Also provided are methods for combating dental caries, erosion, hypersensitivity, and/or staining. The method of use herein includes contacting a subject's dental surfaces and/or oral mucosa with the oral care compositions according to the present disclosure. In some embodiments, the oral care composition is deposited as a protective film. The method of treatment may be by brushing and/or rinsing. Other methods include contacting the toothpaste, tooth gel, dentifrice, tooth powder, prophy paste, mouthwash, rinse, tooth mousse, dental floss, chewing gum, soluble oral care strips or films, or lozenges or other form with the subject's dental surfaces and/or oral mucosa. Depending on the embodiment, the oral care composition may be used as frequently as a toothpaste, or may be used less often, for example, weekly, or used by a professional in the form of a prophy paste or other intensive treatment.

It should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

The present disclosure will further be described by reference to the following examples. The following examples are merely illustrative and are not intended to be limiting. Unless otherwise indicated, all percentages are by weight of the total composition.

EXAMPLES

Example 1. Synthesis of Terpolymer Based on Maleic Acid/Sodium 1-Allyloxy-2-hydroxypropyl-3-sulfonate (SIPOMER COPS 1)/Poly(oxyethylene) Allyl Ether Phosphate (alpha-2-Propen-1-yl-omega-hydroxypoly(oxy-1,2-ethanediyl) phosphate) (SIPOMER PAM 5000)

The following were introduced at room temperature, into a 1 liter reactor, equipped with a mechanical stirrer and a condenser: 65.70 g of a 40 wt. % aqueous maleic acid solution; 24.00 g of a 40 wt. % aqueous solution of SIPOMER COPS 1 (SOLVAY monomer); 42.90 g of a 30 wt. % aqueous solution of SIPOMER PAM 5000 (SOLVAY monomer); and 213.00 g purified water.

After deoxygenation with nitrogen bubbling for 30 minutes, the mixture was brought to 80° C., with agitation. The following was then added separately, in one shot: 4.12 g of a 3 wt % aqueous solution of mercaptoacetic acid, and 25.47 g of a 10 wt % aqueous solution of sodium persulfate. After 60 minutes reaction, 4.12 g of a 3 wt % aqueous solution of mercaptoacetic acid was added in one shot. After another 60 minutes reaction, 4.12 g of a 3 wt % aqueous solution of mercaptoacetic acid, and 25.47 g of a 10 wt % aqueous solution of sodium persulfate were added separately, in one shot. The mixture was then held at 80° C. under agitation for 4 hours. After 6 hours total reaction time at 80° C., the mixture was cooled down to room temperature and transferred.

The number average molecular weight was 3900 g/mol. The theoretical total solids was 12%.

Example 2

Following the procedure of Example 1, the quantities below of the same four ingredients were combined in the stirred, deoxygenated solution and heated to 80° C.: 43.75 g of a 40 wt. % aqueous maleic acid solution; 10.97 g of a 40 wt. % aqueous solution of SIPOMER COPS 1 (SOLVAY monomer); 61.90 g of a 30 wt. % aqueous solution of SIPOMER PAM 5000 (SOLVAY monomer); and 213.00 g purified water.

The mercaptoacetic acid and sodium persulfate aliquots were added as before, at the 1 and 2 hour mark after the first initiator/chain transfer agent addition, the reaction was continued for four more hours, cooled and transferred. An alternative to mercaptoacetic acid is diethyl phosphite $HP(O)(OEt)_2$.

The number average molecular weight was 3780 g/mol. The theoretical total solids was 11.73%.

Example 3. Preparation of Copolymer Solutions

Test Solution 1 was prepared by dissolving 8.3 g of the copolymer solution from Example 1 in 91.7 g of water, to simulate a mouth rinse at 1% by weight polymer. Test Solution 2 was prepared by dissolving 8.5 g of the copolymer solution from Example 2, in 91.5 g of water, to simulate a mouth rinse at 1% by weight polymer.

Test Solution 3 was prepared by dissolving 10 g of Test Solution 2 in 90 g of water, to create a solution at 0.1% by weight polymer with no added salt, i.e. 0 mol/L ionic strength. Test Solution 4 was prepared by dissolving 10 g of Test Solution 2 and 0.87 g of Sodium Chloride in 89.13 g of water, to create a solution at 0.1% by weight polymer with 0.150 mol/L NaCl ionic strength. Test Solution 5 was prepared by dissolving 10 g of Test Solution 2 and 1.72 g of Sodium Chloride in 88.28 g of water, to create a solution at 0.1% by weight polymer with 0.300 mol/L NaCl ionic strength.

Example 4. Adsorption of Polymers on Hydroxyapatite (HA) Surface

Adsorption on hydroxyapatite surfaces was analyzed as a mimic for teeth and bone materials, of the same copolymer in different ionic strength conditions, i.e. Test Solutions 3, 4 and 5 (cf. Example 3). The Quartz Crystal Microbalance with Dissipation Monitoring (i.e. QCM-D) technique was used to estimate the morphology (thickness, viscosity, and elasticity) of the physically adsorbed layer of the copolymer, first in-situ (real time adsorption and desorption of copolymer in water) and after drying. Test Solution 3 allowed determining these parameters in the absence of added salt, while Test solutions 4 and 5 mimicked different physiological conditions comparable to human saliva.

Description of the QCM-D technique can be found in Review of Scientific Instruments 64 (11): 3198-3205, 1993; in Review of Scientific Instruments 67 (9): 3238-3241, 1996 and in Physical Chemistry Chemical Physics 10 (31): 4516-34, 2008.

Test Procedure. Hydroxyapatite (HA) coated QCM sensors (referred to as "HA sensor" in the following) were supplied by Biolin Scientific (Cat/Model#QSX327; Hydroxyapatite sensors, 10 mm). All experiments were carried out at physiological temperature of 37° C. For in-situ QCM-D, a baseline was first set using DI water (0 mM NaCl; pH 7) before the HA sensors were exposed, in separate experiments, to Test Solutions 3, 4 or 5, for up to 15 min to reach a plateau of adsorption indicative of the maximum amount of polymer adsorbed. The flow rate of the test solutions during these in-situ experiments was set at 100 mL/min. Then the polymer treated HA sensors were exposed to deionized water (0 mM NaCl; pH 7) for up to 20 minutes of rinsing, to determine the resilience and removability of the polymer layers deposited. For dry QCM-D, the rinsed samples were dried in air and the areal mass of the deposited polymer was measured in air at 37° C.

Results. In Table 1, in-situ polymer layer thicknesses before and after rinsing with deionized water is provided, and in Table 2, the dry mass deposited as measured after the drying of the coated HA sensors is shown. In-situ and dry QCM results show that the polymer of Test Solution 3 in the lowest ionic strength condition (0 mM NaCl) already adsorbs on HA surface, forming a 1 nm thick copolymer layer (cf. Table 1) and that after the rinsing and drying steps, the areal mass of remaining polymer on hydroxyapatite still has a measurable value (196 ng/cm2, cf. Table 2). The same polymer in higher ionic strength conditions (i.e. Test Solutions 4 and 5, respectively 0.150 and 0.300 mol/L NaCl) increasingly adsorbs on HA surface, forming thicker layers (respectively 3.2 and 5.2 nm, cf. Table 1), increasingly resists rinsing (respectively 2.5 and 3.8 nm, cf. Table 1) and show an increasing areal mass of remaining polymer on HA surface once dried, up to respectively 291 and 421 nano grams/cm$^2$ (i.e. ng/cm$^2$). The polymer of the test solutions therefore reacts positively to higher ionic strength suitable for human physiological conditions.

TABLE 1

QCM-D results of in-situ thickness of the adsorbed layer of polymer from Test Solutions 3, 4 and 5 (cf. Example 3), before and after rinsing with deionized water.

| | Test Solution 3 (0 mol/L NaCl) | | Test Solution 4 (0.150 mol/L NaCl) | | Test Solution 5 (0.300 mol/L NaCl) | |
|---|---|---|---|---|---|---|
| | During exposure | After rinsing | During exposure | After rinsing | During exposure | After rinsing |
| In situ thickness (nm) | 1.0 | <1.0 | 3.2 | 2.5 | 5.2 | 3.8 |

TABLE 2

QCM-D results of dried polymer from Test Solutions 3, 4 and 5 (cf. Example 3).

| | Test Solution 3 (0 mol/L NaCl) | Test Solution 4 (0.150 mol/L NaCl) | Test Solution 5 (0.300 mol/L NaCl) |
|---|---|---|---|
| Dry mass deposited (ng/cm$^2$) | 196 ± 16 | 291 ± 38 | 421 ± 7 |

Example 5. In-Vitro Anti-Stain Testing of Copolymers on Bovine Teeth. Methods Adapted from Those in J. Dent. Res. 61(11):1236, 1982

Tooth Specimen Preparation. Bovine, permanent, central incisors were cut to obtain labial enamel specimens approximately 8×8 mm$^2$. The enamel specimens were then embedded in an auto-polymerizing methacrylate resin so that only the enamel surfaces were exposed. The enamel surfaces were then smoothed on a lapidary wheel and polished with flour of pumice and water. They were then lightly etched to expedite stain accumulation and adherence. The specimens were then scored for pre-test color by means of a Minolta C221, colorimeter, using the L, a* and b* values of the LAB scale. The L a*b* scale is a way of measuring color. In this model, the L score, which is a light (score 100) to dark (score 0) measurement, is most indicative of what one would see on teeth: the higher the L value, the lighter the color of a tooth; the smaller the L value, the more stained the tooth. All teeth had an initial L value around 70 to 80. Based on this score, the specimens were separated into groups of 12 teeth, each group corresponding to the treatment they were going to be exposed to: water alone (reference mimicking no use of mouth rinse); test solution 1 of Example 1 or test solution 2 of Example 2.

Delta E=[(L-L$_o$)$^2$+(a*-a$_o$*)$^2$+(b*-b$_o$*)$^2$]$^{1/2}$ is the overall change of the color of a tooth, L a*b* being the color coordinated after the treatment and L$_o$ a$_o$*b$_o$* those before. Delta L=L-L$_o$, Delta a*=a*-a$_o$* and Delta b=b*-b$_o$* are the individual changes in the color coordinates.

Test Procedure.

The specimens were immersed in pooled human saliva (room temp, slight stirring) for one hour to allow a pellicle film to form. Before the first exposure to a staining broth, they were allowed to sit for a few minutes either in water, test solution 1 or test solution 2, mimicking exposure of teeth to a mouth rinse. They were then removed and allowed to dry for 15 seconds. They were placed in a staining apparatus, consisting of rods rotating and alternately immersing all the specimens in the staining medium or exposing them to air, mimicking the exposure to tea or coffee. Every hour, the specimens were removed from the staining apparatus, patted dry with a towel and the appropriate test solution was reapplied. After drying 15 seconds, the immersion cycles were started up again. This would complete what is referred to as a cycle: a.) exposure to a test solution, b.) alternate exposure to staining broth or air for 1 hour and c.) drying. This continued for up to 4 cycles. At the end of the 4th staining cycle, the specimens were placed in the staining solution overnight on the staining apparatus. The following morning, the specimens were rinsed with water, lightly blotted and scored once again (L a*b*). This first day of treatment mimics a full day alternate exposure to a mouth rinse (or water as a reference) and to staining liquids, without ever brushing the teeth.

Results. The L a*b* color values developed in 4 staining cycles are shown in Table 3. The decrease in the L score of the teeth treated with test solution 2 is smaller (−6.7) than that of the reference water solution (−8.2), indicating that the reference was stained more heavily and the polymer solution successfully retards staining and reduced the darkening of the teeth by close to 20% in comparison to the control (water). Similarly, a* and b* scores increase less with test solution 2 than they do with water, indicating less reddening and yellowing of the teeth. Finally, the overall color change Delta E is −1.9 points smaller with test solution 2 than with water alone. In conclusion, all color metrics after a 1-day stain accumulation were reduced by 20 to 30% with the use of copolymer Test solution 2, versus the use of water.

TABLE 3

Reduction in 1-day Stain Accumulation onto Teeth by Application of Polymers.
Number of cycles of N = 4 {test solution + staining} applications (1st day only)

| Color Coordinate | Water | Test Solution 2 | % change |
|---|---|---|---|
| Delta L | −8.2 | −6.7 | −18% |
| Delta a* | 1.7 | 1.2 | −29% |
| Delta b* | 5 | 3.8 | −24% |
| Delta E | 9.8 | 7.9 | −19% |

Example 6. In-Vitro Stain Removal Testing of Copolymers on Bovine Teeth. Methods Adapted from Those in J. Dent. Res. 61(11):1236, 1982

Accentuated Staining Procedure. After the first day of staining involving 4 staining cycles and an additional overnight exposure to staining broth (Example 4), the same staining procedure was repeated for 4 additional days, 6 cycles per day, for a total of 28 staining cycles without ever brushing the teeth, to accentuate stain accumulation and test the removal of tough stains. The final L a*b* color was recorded on the 6th day after the last overnight immersion in a staining solution, rinsing and drying of the different specimens. Following this stain accumulation, the specimens were brushed with a gentle, low abrasive, commercial dentifrice for 800 strokes (the normal PCR study amount) to determine if the stains that had accumulated during 6 days had any different removal characteristics. Following brushing, the specimens were scored one final time. Percent (%) removal is defined as: % removal= $(L_{after\ brushing}-L_{after\ staining})/(L_{after\ swung}-L_{initial})$ where $L_{initial}$ is the initial L score of the tooth prior to any staining, $L_{after\ staining}$ is the final L score after the 28 cycle-staining procedure and $L_{after\ brushing}$ is the final score once the stained tooth has been brushed. Indeed, $L_{after\ staining}-L_{initial}$ represents the amount of stain deposited over 28 cycles, while $L_{after\ brushing}-L_{after\ staining}$ represents the amount of stain successfully removed by brushing.

Results. The post brushing results are shown in Table 4. The specimens treated with test Solutions 2 show 65% removal of 28-cycle stain accumulation, in comparison to water (reference) which only allows removing 15% of the stain accumulated over the 5 days of staining treatment. Test Solution 1 removes even more, i.e. 76%, providing evidence for further improvement.

TABLE 4

Enhancement of Stain Removal by Pre-treatment of Teeth with Copolymer Solutions Followed by Brushing with Commercial Toothpaste.

| Treatment | % removal |
|---|---|
| Water | −15% |
| Test Solution 1 | −76% |
| Test Solution 2 | −65% |

In view of the above-described Examples, it is expected that daily use of copolymers of the present invention, alone or in combination with phosphate ester surfactants described in U.S. Pat. No. 9,034,308—in a variety of delivery vehicles, such as a toothpaste, tooth gel, dentifrice, tooth powder, prophy paste, mouthwash, rinse, tooth mousse, dental floss, chewing gum, soluble oral care strips or films, or lozenges—would provide a powerful, consumer friendly and easy to use arsenal to correct or prevent a wide range of common oral diseases in both humans and other mammals.

The disclosed subject matter has been described with reference to specific details of particular embodiments thereof. It is not intended that such details be regarded as limitations upon the scope of the disclosed subject matter except insofar as and to the extent that they are included in the accompanying claims.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the exemplary embodiments described herein. The exemplary embodiments described herein illustratively disclosed herein suitably may be practiced in the absence of any element that is not specifically disclosed herein and/or any optional element disclosed herein.

While compositions and methods are described in terms of "comprising," "containing," or "including" various components or steps, the compositions and methods can also "consist essentially of" or "consist of" the various components, substances and steps. As used herein the term "consisting essentially of" shall be construed to mean including the listed components, substances or steps and such additional components, substances or steps which do not materially affect the basic and novel properties of the composition or method. In some embodiments, a composition in accordance with embodiments of the present disclosure that "consists essentially of" the recited components or substances does not include any additional components or substances that alter the basic and novel properties of the composition. If there is any conflict in the usages of a word or term in this specification and one or more patent or other documents that may be incorporated herein by reference, the definitions that are consistent with this specification should be adopted.

We claim:

1. An α, β-ethylenically unsaturated maleimide phosphate compound of the formula (B):

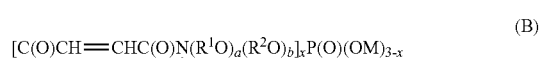

wherein
R$^1$ is a substituted or unsubstituted (C$_2$-C$_4$) alkylene moiety;
R$^2$ is a substituted or unsubstituted (C$_2$-C$_4$) alkylene moiety;
M is identical or different, hydrogen, alkali metal, ammonium, protonated alkyl amine, protonated alkanolamine, or protonated basic amino acid;

X is 1 or 2, a is from 1 to 20; and b is from 0 to 20.

2. A composition comprising a copolymer polymerized from a monomer mixture comprising one or more α, β-ethylenically unsaturated maleimide phosphate compounds of claim 1 and one or more other α, β-ethylenically unsaturated compounds, at least one of which is other than maleimide-functional.

3. An oral care composition in the form of a toothpaste, tooth gel, dentifrice, tooth powder, prophy paste, mouthwash, rinse, tooth mousse, dental floss, chewing gum, soluble oral care strip or film for direct application or attachment to an oral surface, or lozenge for combating dental caries, erosion, hypersensitivity, and/or staining comprising an orally acceptable carrier and a composition according to claim 2.

4. A method for combating dental caries, erosion, hypersensitivity, and/or staining comprising contacting a dental surface with the oral care composition of claim 3.

* * * * *